(12) United States Patent
Cong et al.

(10) Patent No.: US 8,805,537 B1
(45) Date of Patent: Aug. 12, 2014

(54) HYBRID PACKING FOR IMPLANTABLE DEVICE

(71) Applicant: Medtronic, Inc., Minneapolis, MN (US)

(72) Inventors: Peng Cong, Plymouth, MN (US); Bernard Li, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/799,860

(22) Filed: Mar. 13, 2013

(51) Int. Cl.
*A61N 1/00* (2006.01)

(52) U.S. Cl.
USPC ........................................ 607/116

(58) Field of Classification Search
USPC ........................................ 607/116
See application file for complete search history.

(56) References Cited

U.S. PATENT DOCUMENTS

| | | | |
|---|---|---|---|
| 3,727,616 A * | 4/1973 | Lenzkes | 607/59 |
| 8,433,409 B2 | 4/2013 | Johnson et al. | |
| 2005/0075694 A1 | 4/2005 | Schmeling et al. | |
| 2005/0075696 A1 | 4/2005 | Forsberg et al. | |
| 2005/0075697 A1 | 4/2005 | Olson et al. | |
| 2005/0075698 A1 | 4/2005 | Phillips et al. | |
| 2005/0075699 A1 | 4/2005 | Olson et al. | |
| 2005/0075700 A1 | 4/2005 | Schommer et al. | |
| 2005/0113887 A1 | 5/2005 | Bauhahn et al. | |
| 2007/0236861 A1 | 10/2007 | Burdon et al. | |
| 2007/0244520 A1 * | 10/2007 | Ferren et al. | 607/2 |
| 2012/0003531 A1 | 1/2012 | Howard et al. | |
| 2012/0188096 A1 | 7/2012 | Corndorf et al. | |

* cited by examiner

*Primary Examiner* — Robert N Wieland
(74) *Attorney, Agent, or Firm* — Shumaker & Sieffert, P.A.

(57) ABSTRACT

Described herein is a device configured to be implanted into a live human or animal. The device includes an electrically non-conductive frame; one or more electrical components disposed in the electrically non-conductive frame; and a self-supporting film. The self-supporting film forms a hermetical seal with the electrically non-conductive frame. The self-supporting film and the frame enclose the electrical components. The device is configured to be implanted into a live human or animal. Also described herein is a method of making a device configured to be implanted into a live human or animal. The method includes providing an electrically non-conductive frame comprising one or more feedthroughs, openings and a cavity; disposing electrical components within the cavity; optionally filling the cavity with a material to embed the electrical components in the material; and sealing the openings by applying a self-supporting film to the one or more openings.

30 Claims, 8 Drawing Sheets

HYBRID PACKING FOR IMPLANTABLE DEVICE

TECHNICAL FIELD

The disclosure herein relates to implantable medical device and packaging of such device.

BACKGROUND

In the context of implantable device, the packaging, which may sometimes be referred to as the housing, or "can" of the implantable device, is a component of the implantable device, and includes an interface between the implantable device and the host. Packaging of implantable device may also provide a substrate such as a frame onto which other components of the implantable device may be mounted. Typically, packaging for implantable device serves at least two functions. First, the packaging protects the host in which the device is implanted. Second, the packaging protects internal components of the device from surrounding tissues of the host.

Packaging has been made of metallic materials such as Ti and Ti alloys. These materials provide good bio-compatibility but are bulky and expensive. Metallic materials also hinder the non-contact recharging of batteries that may exist in the implantable device.

Alternative packaging materials such as ceramic are also possible but have their own limitations. For example, ceramic packaging is still bulky and lack ductility, although ceramic packaging allows non-contact recharging.

Packaging is preferably compatible with feedthroughs. Feedthroughs are used to accommodate signal pathways between the implantable device and the host. For example, an implantable defibrillator has feedthroughs to detect fibrillation of the heart of the host and to send an electric pulse to the heart to defibrillate it.

SUMMARY

Described herein is a device, comprising: an electrically non-conductive frame; one or more electrical components disposed in the electrically non-conductive frame; and at least a self-supporting film; wherein the self-supporting film forms a hermetical seal with the electrically non-conductive frame, wherein the self-supporting film and the frame enclose the electrical components, and wherein the device is configured to be implanted into a live human or animal.

According to an embodiment, the frame comprises one or more openings.

According to an embodiment, the frame is ceramic, plastic or polymer composite.

According to an embodiment, the frame comprises one or more feedthroughs, wherein the one or more feedthroughs are functional to accommodate signal pathways between the device and the live human or animal.

According to an embodiment, the self-supporting film seals the one or more openings.

According to an embodiment, the self-supporting film is water impermeable.

According to an embodiment, exposed surfaces of the self-supporting film are bio-compatible.

According to an embodiment, the self-supporting film is uniform in composition or is a composite.

According to an embodiment, the self-supporting film has a layered structure having two or more distinct layers.

According to an embodiment, the self-supporting film comprises parylene C, silicone or a combination thereof.

According to an embodiment, the self-supporting film comprises an adhesive layer.

According to an embodiment, the self-supporting film is electrically non-conductive.

According to an embodiment, the self-supporting film is flexible.

According to an embodiment, the electrical components comprise a battery.

According to an embodiment, the electrical components comprise a coil, an antenna, a modem, or a combination thereof.

According to an embodiment, the electrical components are configured to recharge the battery.

According to an embodiment, the electrical components are configured to receive signals from and/or transmit signals from the device to devices outside the live human or animal.

According to an embodiment, the electrical components are embedded in a material.

According to an embodiment, the material is thermally conductive.

According to an embodiment, the device is entirely coated with a coating except the one or more feedthroughs.

According to an embodiment, the coating is bio-compatible.

According to an embodiment, the device comprises a surface with an area less than 2 $cm^2$.

According to an embodiment, the device is injectable into the live human or animal through a syringe.

Also disclosed herein is a method of making a device configured to be implanted into a live human or animal, comprising: providing an electrically non-conductive frame comprising one or more feedthroughs, one or more openings and a cavity; disposing one or more electrical components within the cavity; optionally filling the cavity with a material to embed the electrical components in the material; and sealing the one or more openings by applying a self-supporting film to the one or more openings.

According to an embodiment, self-supporting film is applied layer by layer.

According to an embodiment, the method further comprises coating the device except the one or more feedthroughs.

BRIEF DESCRIPTION OF FIGURES

The disclosure herein generally relates to a hybrid packaging, or "can", of an implantable device, which preferably provides protection to the host, protection to the device itself, small size, low cost, ductility, possibility of non-contact recharging, compatibility with feedthroughs, or a combination of any of these properties.

DETAILED DESCRIPTION

One example of an implantable device is an implantable neurostimulator. An implantable neurostimulator may be used to deliver therapy to patients to treat a variety of symptoms or conditions such as chronic pain, tremor, Parkinson's disease, epilepsy, incontinence, sexual dysfunction, or gastroparesis. In general, the neurostimulator delivers neurostimulation therapy in the form of electrical pulses or continuous waveforms. Depending on the application for which they are implanted in a patient, neurostimulators may include a variety of electrical and/or mechanical components, A neurostimulator may include rigid packaging that houses all of its components, which are generally fragile, to protect the components from forces to which they would otherwise be exposed when implanted within the human body. The size and shape of a neurostimulator packaging is dependent on the sizes and shapes of the components of the neurostimulator. As used herein, the term "patient" and the term "host" are interchangeable and may refer to a live human or a live animal.

One type of neurostimulator delivers neurostimulation therapy via one or more leads that include electrodes located proximate to the spinal cord, pelvic nerves, or stomach, or within the brain of a patient, and located away from the neurostimulator. This type of neurostimulator may be implanted, for example, within the abdomen, upper pectoral region, or subclavicular region of a patient. Leads or catheters may be used to deliver therapy or monitor a physiological parameter at a remote location of the host. The leads or catheters extend from the neurostimulator packaging for placement at a target site. Implantation and positioning of leads and catheters can be difficult and time-consuming from the perspective of a surgeon, particularly where the neurostimulator is located a significant distance from the treatment or monitoring site. The increased surgical time, increased surgical trauma, and increased amount of implanted material associated with the use of leads and catheters can increase the risk to the patient of complications associated with the implantation of a neurostimulator. In addition, selection of an efficacious target site for deployment of a lead or catheter is difficult. Some leads include an array of electrodes that can be selectively activated to target different nerve sites or create different energy fields. Once a lead is in place, however, repositioning of the lead is generally undesirable. In particular, the patient ordinarily must undergo an additional surgical procedure with associated risks. Accordingly, selection of a nerve site appropriate for therapeutic efficacy continues to be a concern.

Another type of neurostimulator is "leadless," namely having electrodes located on the packaging of the neurostimulator. This type of neurostimulator is preferably small and can be placed directly in proximity to a target site, by surgery or injection.

Figure 1:
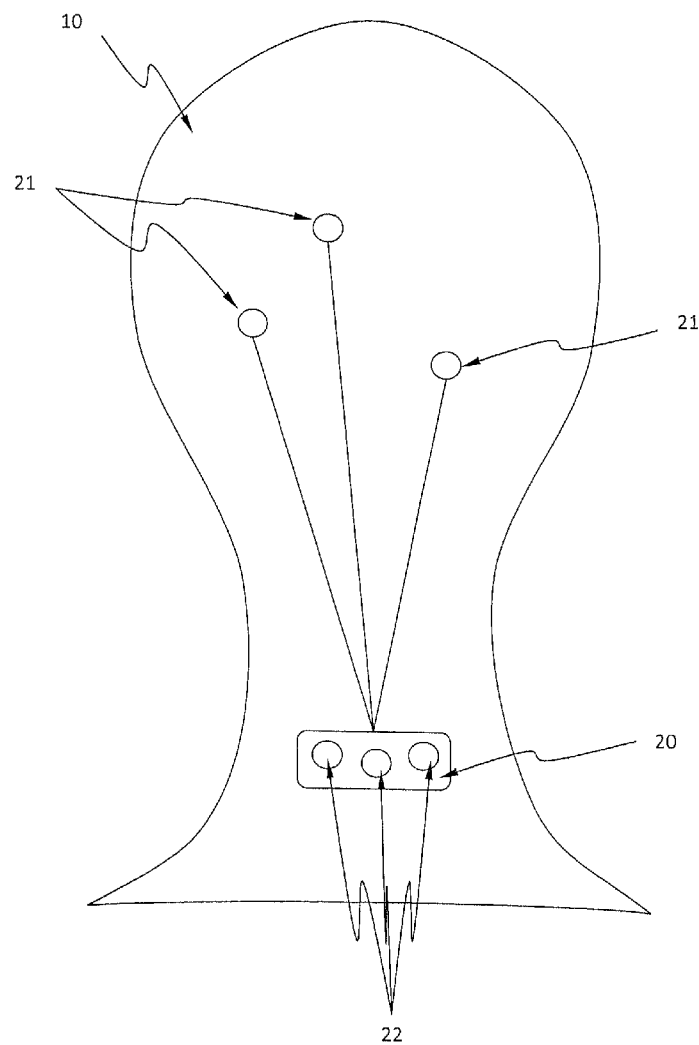
FIG. 1 illustrates an implantable medical device system within a human body, in accordance with various aspects and principles of the present disclosure.

FIG. 1 is a simplified schematic view of a neurostimulator 20. The neurostimulator 20 is implanted into a human host 10. The neurostimulator 20 may be connected to leads 21 located away from the neurostimulator 20. The neurostimulator 20 may be leadless and has electrodes 22 located directly on the packaging of the neurostimulator 20.

Figure 2:
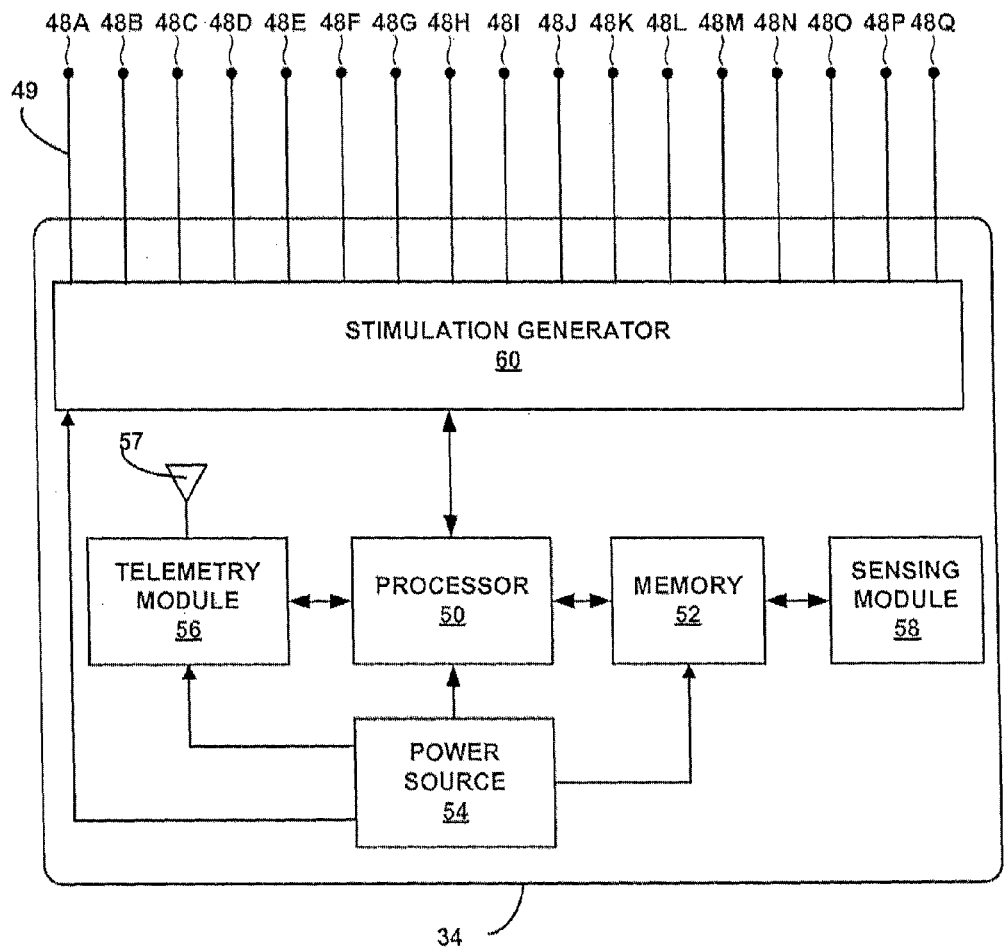
FIG. 2 is a functional block diagram illustrating various components of an exemplary implantable device.

FIG. 2 is a functional block diagram illustrating various components of an exemplary implantable device 34 such as a neurostimulator 20. Implantable device 34 includes processor 50, memory 52, power source 54, telemetry module 56, antenna 57, sensing module 58, and stimulation generator 60. Implantable device 34 is also shown in FIG. 2 coupled to each of the electrodes 48A-48Q (collectively "electrodes 48") via a respective conductor 49. In some examples, two or more electrodes 48 may be coupled to stimulation generator 60 via a common conductor. Electrodes 48A-48P may be implantable and may be deployed on one or more implantable leads. Alternatively, some or all of electrodes 48 may be entirely disposed on the packaging of the implantable device 34, and electrically coupled to stimulation generator 60 via conductors entirely encompassed in the packaging.

Memory 52 may store instructions for execution by processor 50, stimulation therapy data and/or other information regarding therapy for the host. Processor 50 may control stimulation generator 60 to generate and deliver stimulation according to a selected one or more of a plurality of therapy programs or program groups stored in memory 52. Each stored therapy program defines a particular set of electrical stimulations parameters, such as a stimulation electrode combination or configuration, current or voltage amplitude, frequency (e.g., pulse rate in the case of stimulation pulses), and pulse width. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 34 in this disclosure.

In some examples, information stored by memory 52 may include information regarding therapy that the host had previously received or information regarding a current therapy regimen. Storing both historical and current therapy information may be useful for subsequent therapy such that, for example, a clinician may retrieve the stored information to determine the therapy applied to the host during a previous therapy session. The information stored in memory 52 may also include, for example, information regarding the brain or other anatomical structures associated with host condition and the corresponding stimulation therapy program defined by stimulation therapy parameter values, where applying the stimulation therapy program helps control the anatomical structures of the brain (in the example of deep brain stimulation therapy) to achieve a desired therapeutic outcome for the associated host condition.

Processor 50 may include one or more microprocessors, digital signal processors (DSPs), application-specific integrated circuits (ASICs), field-programmable gate arrays (FPGAs), or other digital logic circuitry. Functions attributed to processors described herein may be embodied in a hardware device via software, firmware, hardware, or any combination thereof. Processor 50 controls operation of implantable device 34, e.g., controls stimulation generator 60 to generate and deliver stimulation therapy according to a selected therapy program or group of therapy programs retrieved from memory 52. For example, processor 50 may control stimulation generator 60 to deliver electrical signals, e.g., as stimulation pulses or continuous waveforms, with current or voltage amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program, processor 50 may control stimulation generator 60 to deliver stimulation according to the selected therapy program or programs in the groups, e.g., simultaneously or on a time-interleaved basis. A group may include a single therapy program or multiple therapy programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and status of the electrodes. The electrode combination may specify particular electrodes in a single array or multiple arrays, and on a single lead or among multiple leads.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50. Stimulation generator 60 can be a single channel or multi-channel stimulation generator. For example, stimulation generator 60 may be capable of delivering a single stimulation pulse, multiple stimulation pulses, or a continuous signal at a given time via a single electrode combination or multiple stimulation pulses at a given time via multiple electrode combinations.

In some examples, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses (e.g., in a pulse-based system) based on signals from processor 50.

Sensing module 58 may be configured to sense a physiological parameter of the host, such as a bioelectrical brain signal within the host's brain (e.g., local field potentials (LFPs), electroencephalogram (EEG) signals and electrocortiogram (ECoG) signals, or a broader genus of electrical signals within the brain). Sensing module 58, under the control of processor 50, may sense bioelectrical signals or another signal indicative of a host parameter and provide the sensed signals to processor 50. To sense bioelectrical brain signals, processor 50 may control sensing module 58 to selectively sense bioelectrical brain signals with sub-combinations of electrodes 48A-48P. In this manner, implantable device 34 may be configured such that sensing module 58 may sense bioelectrical signals with different combinations of electrodes 48A-48P. Although sensing module 58 is incorporated into a common housing with stimulation generator 60 and processor 50 in the example shown in FIG. 2, in other examples, sensing module 58 may be in a physically separate housing from implantable device 34 and may communicate with processor 50 via wired or wireless communication techniques.

Sensing module 58 may receive the bioelectrical signals from electrodes 48A-48P or other electrodes positioned to monitor brain signals of the host. Processor 50 may receive the output of sensing module 58, which may be raw bioelectrical signals. In other examples, processor 50 may apply additional processing to the bioelectrical signals, e.g., convert the signals to digital values for further processing, filter the signals, and the like. In some examples, sensing module 58 may include circuitry such as, for example, a pressure sensor, a pulse oximeter, and the like for sensing other physiological characteristics in addition to, or instead of, bioelectric signals (e.g., bioelectric signals from the brain).

Telemetry module 56 supports wireless communication between implantable stimulator 34 and an external programmer and/or another computing device. Telemetry module 56 may include a RF transceiver to permit bi-directional communication between implantable device 34 and the external programmer and/or computing device. In one example, telemetry module 56 may utilize other communication protocols and a corresponding transceiver, for example, a Bluetooth® transceiver for telemetry using the Bluetooth® protocol. Telemetry module 56 may include an antenna 57 that may take on a variety of forms. For example, antenna 57 may be formed by a conductive coil or wire embedded in the packaging of the implantable device 34. Instead or in addition to the conductive coil or wire, antenna 57 may be mounted on a circuit board carrying other components of implantable device 34 or take the form of a circuit trace on the circuit board. In this way, telemetry module 56 may permit communication with the external programmer and/or computing device, to receive, for example, new programs or program groups, or adjustments to programs or program groups.

Telemetry module 56 may also communicate information regarding previous therapy sessions that have been stored in memory 52, to an external programmer during a subsequent therapy session; the information regarding a previous therapy session may have been imported by a programmer used in the previous session. The stored information may include, for example, lead placement in the host, stimulation therapy parameter values, desired therapy outcome defined by the user for a particular program, host information, clinic(s) where the host had previously received treatments, previous clinician information, and the like.

Power source 54 may be a non-rechargeable primary cell battery or a rechargeable battery and may be coupled to power circuitry. However, the disclosure is not limited to examples in which the power source is a battery. In another example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within implantable device 34. In some examples, power requirements may be small enough to allow implantable device 34 to utilize host motion at least in part and implement a kinetic energy-scavenging device to trickle charge a rechargeable battery. A voltage regulator may generate one or more regulated voltages using the battery power.

Figure 3A:
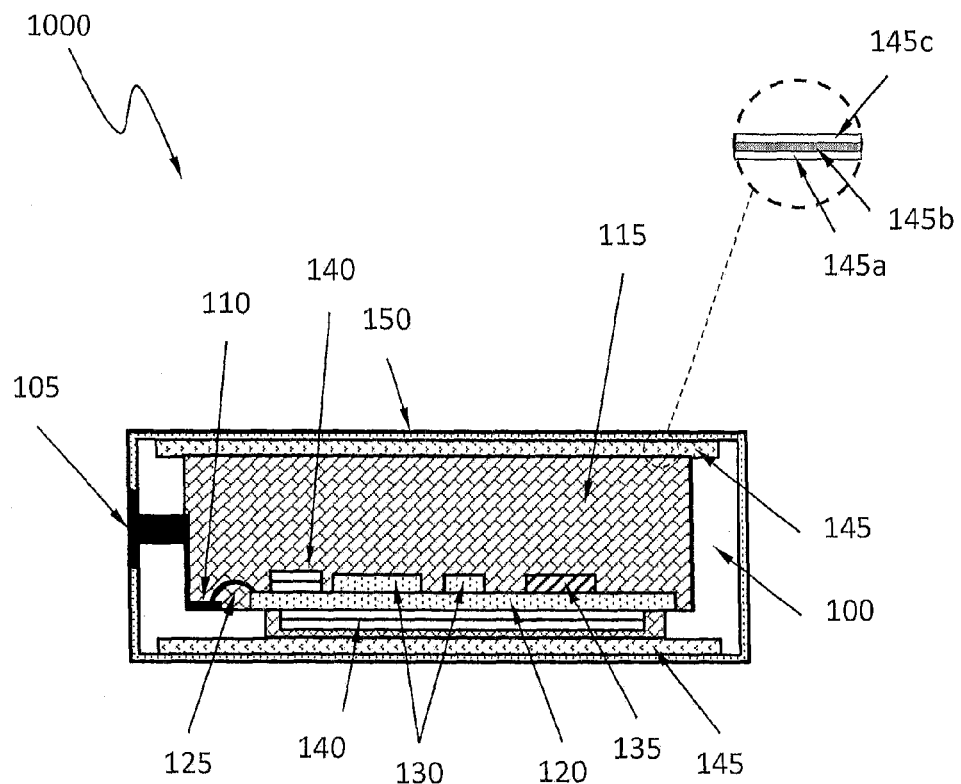
FIG. 3A depicts a schematic diagram of an implantable device, in accordance with various aspects and principles of the present disclosure.

FIG. 3A depicts a schematic view of implantable device 1000. The implantable device 1000 includes a frame 100. The frame 100 provides mechanical support of the entire device 1000. According to an embodiment, the frame 100 is electrically non-conductive. For example, the frame 100 comprises an electrically non-conductive material, such as ceramic, plastic (e.g., PEEK), or polymer composite (e.g., polymer matrix embedded with ceramic powder or graphite powder).

The polymer composite may have ceramic reinforcement therein. In another example, the frame 100 may comprise one or more alloys with high electrical resistivity such as $TiAl_6V_4$, $TiAl_6Nb_7$, etc. In embodiment, the frame 100 is free from an electrically conductive coating.

The frame 100 may be configured with one or more feedthroughs 105, the feedthroughs 105 being electrically connected to one or more electrical contacts 110. The feedthroughs 105 may be electrically conductive and are configured to accommodate signal pathways between the implantable device 1000 and the host in which the implantable device 1000 may be implanted. The feedthroughs 105 and contacts 110 may be formed using any suitable technique, such as, for example, co-firing. Details of co-firing may be found in commonly assigned U.S. patent application Ser. No. 11/278,773, the disclosure of which is hereby incorporated by reference to the extent that the disclosure does not conflict with the current disclosure.

Internal components of the implantable device 1000 may be mounted onto the frame 100 by any suitable technique such as, for example, soldering, adhesive contact, etc. For example, the internal components may comprise a substrate 120 such as a printed circuit board (PCB), with electronic components 130, such as integrated and/or discrete components, mounted on the substrate 120. In an embodiment, the substrate 120 is a flexible substrate such as polyimide, PEEK or transparent conductive polyester film that can support electronic components thereon.

The internal components may also comprise battery 135 or another power source, such as one or more super capacitors. The battery 135 may be rechargeable. Details of the battery 135 may be found in commonly assigned applications such as U.S. patent application Ser. Nos. 12/696,890 and 13/231,408, the disclosures of which are hereby incorporated by reference to the extent that the disclosures do not conflict with the current disclosure.

In some examples according to the current disclosure, the internal components need not comprise a power source. For instance, a power source external to the patient may transfer energy transcutaneously to components of the implantable device 1000 such as a coil of the implantable device. This energy may be transferred substantially continuously in some examples, and may be used to power operation of the device without use of any power source.

An electrical connection 125 may be made between contacts 110 and the internal components. Although the electrical connection 125 is depicted as a piece of wire, it can be any suitable connection.

Internal components of implantable device 1000 may also comprise one or more recharging and telemetry components 140. Although recharging and telemetry circuitry is depicted together for ease of reference, it is understood that recharge and telemetry components may comprise both a recharge coil, dedicated recharge circuitry, a separate telemetry coil or other antenna, and telemetry circuitry. In another embodiment, a single coil may be used to both receive recharge energy and to send/receive information between the implantable device 1000 and an external device such as a programmer or recharger.

The recharging and telemetry components 140, could be positioned all on the same side of the substrate 120 with the electronic components 130. Alternatively, one or more of a recharging coil, a telemetry coil or other telemetry antenna, and/or related circuitry may be positioned on the opposite side of the substrate 120 from the electronic components 130, and coupled to the electronic components 130 through vias in the substrate 120. The recharging and telemetry components 140 may include one or more of a coil, antenna, modem, etc. The recharging and telemetry components 140 may be electrically connected to the electronic components 130 and/or the battery 135. The recharging and telemetry components 140 may function to receive signals from and/or transmit signals to devices outside the host, for purposes such as controlling, monitoring, and collecting data from the implantable device 1000. The recharging and telemetry components 140 may comprise any unit or mechanism capable of facilitating wireless data transfer between the implantable device 1000 and an external device, in which the external device may comprise an external medical device, a programming device, a remote telemetry station, a physician-activated device, a patient-activated device, a display device, or any other type of device capable of sending and receiving signals to and from the implantable device 1000. To this end, the recharging and telemetry components 140 may be configured to perform any type of wireless communication. For example, the recharging and telemetry components 140 may send and receive radio frequency (RF) signals, infrared (IR) frequency signals, or other electromagnetic signals. That is, any variety of modulation techniques may be used to modulate data on a respective electromagnetic carrier wave. Alternatively, the recharging and telemetry components 140 may use sound waves for communicating data, or may employ the patient's tissue as the transmission medium for communicating with a device, such as a programmer positioned on the patient's skin. An example of the recharging and telemetry components 140 may be found in commonly assigned U.S. patent application Ser. No. 13/429,841, the disclosures of which are hereby incorporated by reference to the extent that the disclosures do not conflict with the current disclosure.

The recharging and telemetry components 140 may also function to recharge the battery 135 by receiving energy transcutaneously through the packaging of the implantable device 1000 from an external power source. For example, an external power source may be positioned outside the host in proximity to the recharging and telemetry components of the implantable device 100. The power source comprises an external antenna and electronics configured to drive a coil in the antenna with an oscillating current in order to induce a current in a coil in the recharging and telemetry components 140. Examples of the power source may be found in U.S. Patent Publication Nos. 2005/0113887, 2005/0075700, 2005/0075699, 2005/0075698, 2005/0075697, 2005/0075696, 2005/0075694, and 2005/0075693, all disclosure of which is incorporated herein by reference to the extent the disclosures do not conflict with the current disclosure. It will be appreciated that the term "recharge" as used herein refers to any type of charge including, but not limited to, an initial charge and a subsequent charging event (i.e., recharging). Recharging may comprise close-range (proximity) recharge accomplished by inductance between the external coil and a coil of recharge and telemetry components 140 when the coils are relatively close together (e.g., less than a foot apart). Alternatively or additionally, recharging may comprise transfer of energy when the external and internal coils are farther apart such that the transfer of energy occurs via RF waves.

Returning to FIG. 3A, the internal components may be embedded in material 115. For example, material 115 may be epoxy or other elastic material such as silicone. For example, material 115 may be a polymer composite material such as epoxy with carbon fibers, graphite particles, titanium oxide, and/or silicon nitride particles embedded therein. A polymer composite material may reduce thermal shrinkage and increase thermal conductivity of the material 115. The material 115 preferably is electrically non-conductive. The material 115 preferably has high thermal conductivity, low coefficient of thermal expansion, and low shrinkage during curing.

Any exposed internal component and any exposed portion of material 115 may be sealed by film 145. A film and a coating are distinct in that a film is self-supporting, i.e., not supported by a substrate; while a coating is applied onto a substrate and cannot be self-supporting. For example, a film may be at least about 100 µm in thickness (e.g., 200-400 µm in thickness) to be self-supporting; a coating can be much thinner (e.g., 30 µm in thickness or thinner). The film 145 and frame 100 may form a hermetical seal, thereby preventing direct contact of the internal components and the material 115 with tissues of the host. The film 145 is essentially water impermeable. The film 145 thus functions as a water barrier to protect the internal components from water in the host. Exposed surfaces of film 145 are bio-compatible. The film 145 thus protects the host from the device 1000. The film 145 may be uniform in its composition or a composite and may also be a layered structure having two or more distinct layers. For example, the film 145 may comprise a water barrier layer 145b (e.g., thickness from 10-200 µm) made of a water impermeable material such as parylene C; the film 145 may comprise a bio-compatible layer 145c made of a bio-compatible material such as silicone (e.g., thickness from 50-200 µm); the film 145 may comprise an adhesive layer 145a that can form a hermetical seal with the frame 100. In some examples, one or more layers of the film 145 may be created using a deposition process such as sputtering. The adhesive layer 145a may be polyurethane or silicone. In one specific example, an outer layer of the film could include a layer of sputtered ceramic. The film 145 may have more than three layers. The layers of the film 145 may be bonded together thermally, by adhesive, by chemical bonds, by physical bonds or a combination thereof. The film 145 is preferably electrically non-conductive, and thus allows telemetry and recharging of the device 1000. The film 145 is preferably flexible.

The water barrier layer 145b itself may have multiple layers such as PP/EVAL/PP, or PP/EVAL/PET, or HDPE/EVA/PVDC/EVA, wherein PP is polypropylene; EVAL is ethylene vinyl alcohol; PET is polyethylene terephthalate; HDPE is high-density polyethylene; EVA is ethylene vinyl acetate; and PVDC is polyvinylidene chloride. These multiple layers within the water barrier layer 145b may be pressed together. In one example, multiple layers may be pressed while being heated to fuse them to form a film. The film may be then cut to size to form the film 145. Although these examples are given, those skilled in the art will appreciate that the layers may be arranged in other combinations besides those listed herein, which are merely illustrative. The water barrier layer 145b may have a thickness from 10 to 500 microns, preferable microns. As one particular example, the water barrier layer 145b has a thickness of about 150 microns. The layers of the film 145 do not have to be the same thickness. Allowing different thicknesses would allow tailoring for the functionalities of the layers.

The water barrier layer 145b may further comprise a metal layer, wherein the metal layer has an electrical resistivity greater than 40 µΩ·cm.

The entire device 1000 may be coated with coating 150 except the feedthroughs 105. The coating 150 is bio-compatible and can further improve the bio-compatibility and reliability of the device 1000.

Figure 3B:
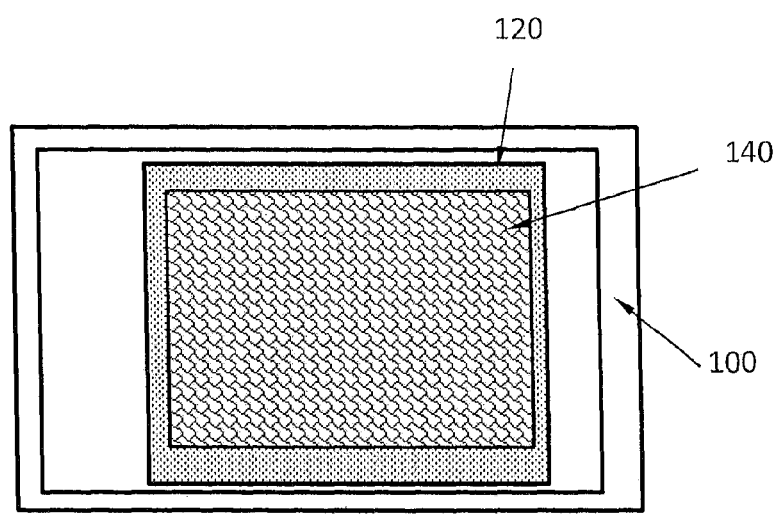
FIG. 3B shows a bottom view of the implantable device of FIG. 3A.

FIG. 3B shows a bottom view of the implantable device 1000, with material 115, film 145, coating 150 hidden, in order to show at least one of the recharging and telemetry components 140 positioned on the opposite side of the substrate 120 from the electronic components 130.

Figure 4A:
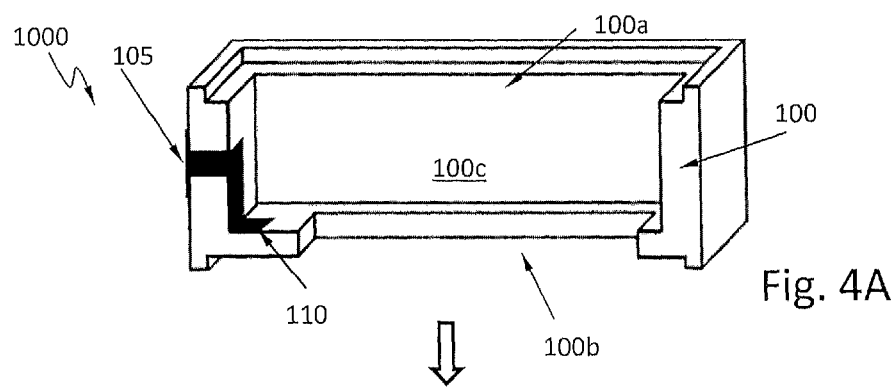
FIGS. 4A-4E show an exemplary method of making the device of FIG. 3A, in accordance with various aspects and principles of the present disclosure.
Figure 4B:
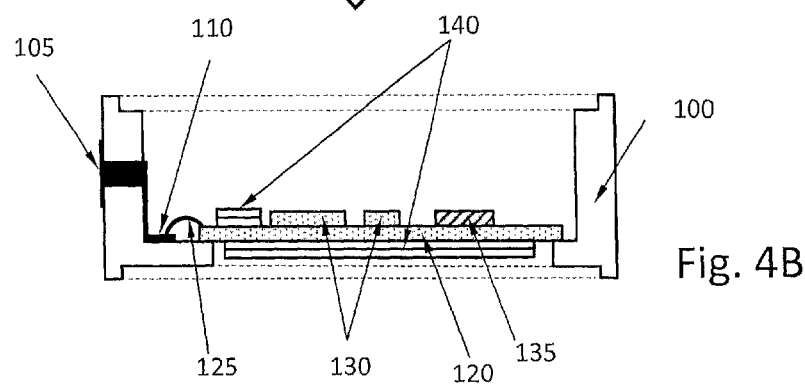
Figure 4C:
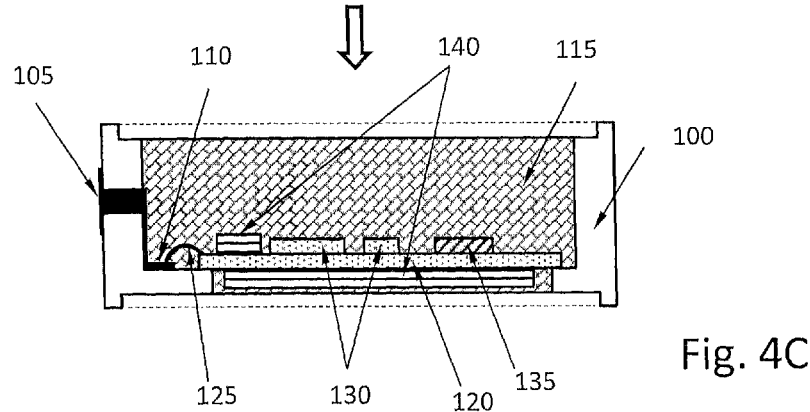
Figure 4D:
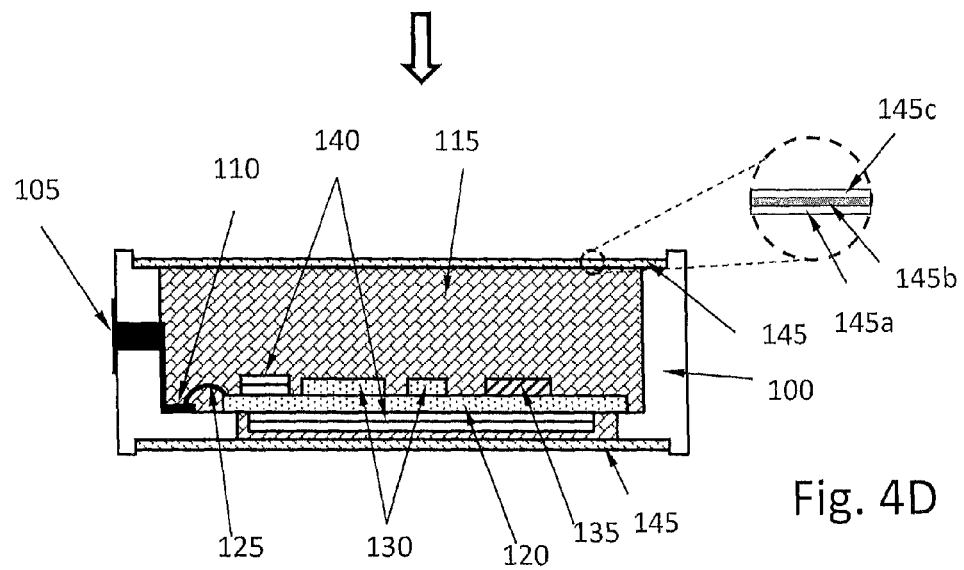
Figure 4E:
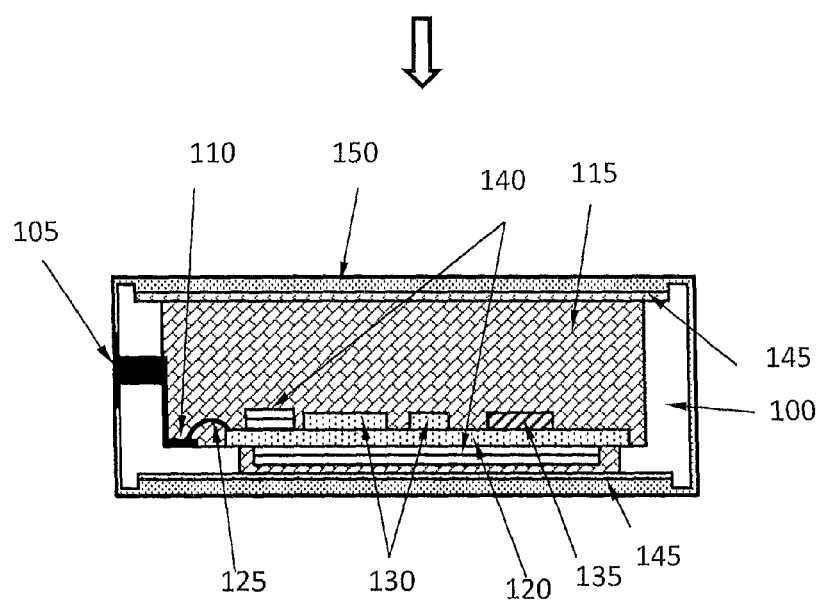

FIGS. 4A-4E illustrate an exemplary method of making the device 1000, according to an embodiment. FIG. 4A shows a cut-away perspective view of the device 1000. FIGS. 4B-4E show only the cut-away cross section in FIG. 4A for brevity. As depicted, frame 100 may have openings, such as 100a and 100b for installing the internal components through such openings. The frame 100 may contain cavity 100c for accommodating the internal components. The internal components such as substrate 120, electronic components 130, battery 135, and recharging and telemetry components 140 are installed into cavity 100c and fixed to frame 100 by any suitable methods such as using adhesive, brazing, soldering, mechanical force, etc. The internal components may include contacts pads for electrical connections to feedthroughs 105 and contacts 110. Electrical connections between the contacts pads, feedthroughs 105 and contacts 110 may be formed by any suitable method.

The cavity 100c may be then filled with material 115 using any suitable method, such as pouring precursors of material 115 into the cavity 100c followed by curing via heat or ultra-violet light. A degassing process, may be using before curing to eliminate essentially all moisture, air bubbles, and air cavities in the cavity 100c. This degassing process may allow material 115 to more readily flow into small areas between components. In other cases, it may be desirable to omit one or more of the filling and degassing steps. The openings, such as 100a and 100b, are then sealed using film 145. The film 145 may be applied layer by layer, especially when film 145 comprises distinct layers such as 145a-145c. The film 145 may also be applied with all the layers already pressed together. For example, the layers may be thermally pressed to form a film, which is then cut into size to form the film 145, and applied to the frame. The film 145 may be applied by adhering film 145 onto the frame 100 and/or heating. In one case, a fixture that operates like an iron may be pressed against the areas of film 145 that contact frame 100 to perform this heating. This type of operation may use a combination of heat and pressure to affix film 145 to frame 100. In any examples involving heating of this kind, the heat applied to the frame 100 and/or film 145 must be maintained below temperatures that will damage components of the implantable device 1000. In still other examples, a fixture may be pressed against the areas of film 145 that contact frame 100 to use pressure alone to cause an adhesive layer of film to become affixed to frame.

Preferably, applying the film 145 to the frame 100 does not expose the frame 100 to temperatures above 150° C. In some cases, additional adhesive material may be applied to frame prior to affixing film 145 to frame to aid in forming the bond between film 145 and frame 100. The additional adhesive material may be a medical grade adhesive such as polyurethane or silicone. Thus, various combinations of heat, pressure, and/or adhesive may be used to cause the film 145 may form a hermetical seal with frame 100. The entire device 1000 may optionally be coated with coating 150.

Figure 5:
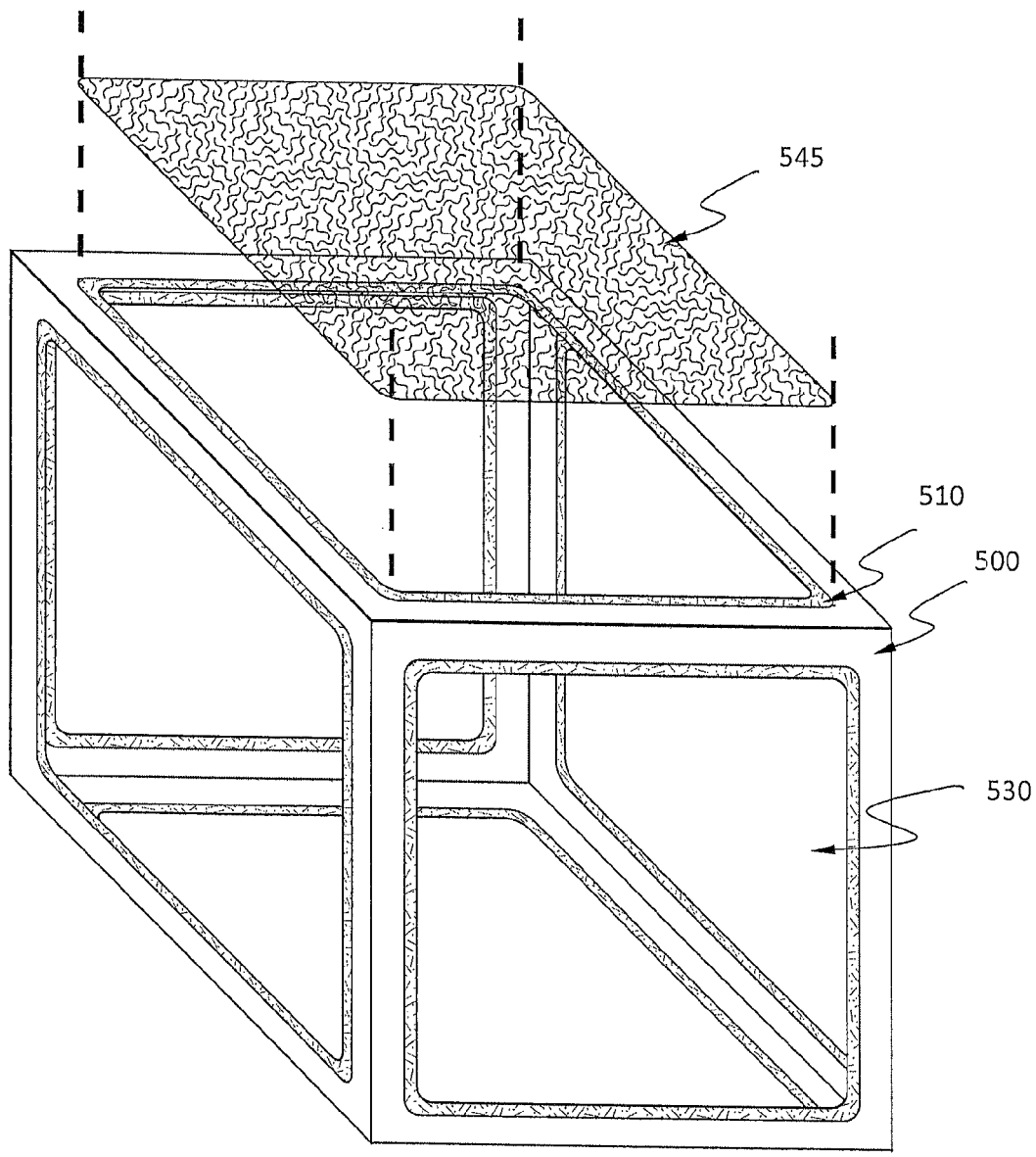
FIG. 5 depicts a schematic diagram of an implantable device, in accordance with various aspects and principles of the present disclosure.

FIG. 5 shows a frame 500 of an implantable device. The frame 500 may be a polyhedron such as a cube. Frame 500 may be formed of materials, and using any of the techniques, shown and described in reference to frame 100 of the embodiment of FIGS. 3A and 3B. A face of the frame 500 may have an opening 530 and a ledge 510 that may be recessed from the face. The ledge 510 may be configured to receive a film 545 such as the film 145 described herein. The film 545 and frame 500 may form a hermetical seal, thereby preventing direct contact of the internal components mounted in frame 500 from water in the host. In the example shown in FIG. 5, each of the sides of the frame 500 may be fitted to receive a respective film portion. Thus, in the example, film 545 may be provided to all six sides of the cube in any of the ways described herein. Thus, an implantable device may have any number of openings that are covered by film as is shown further in regards to FIG. 6.

Figure 6:
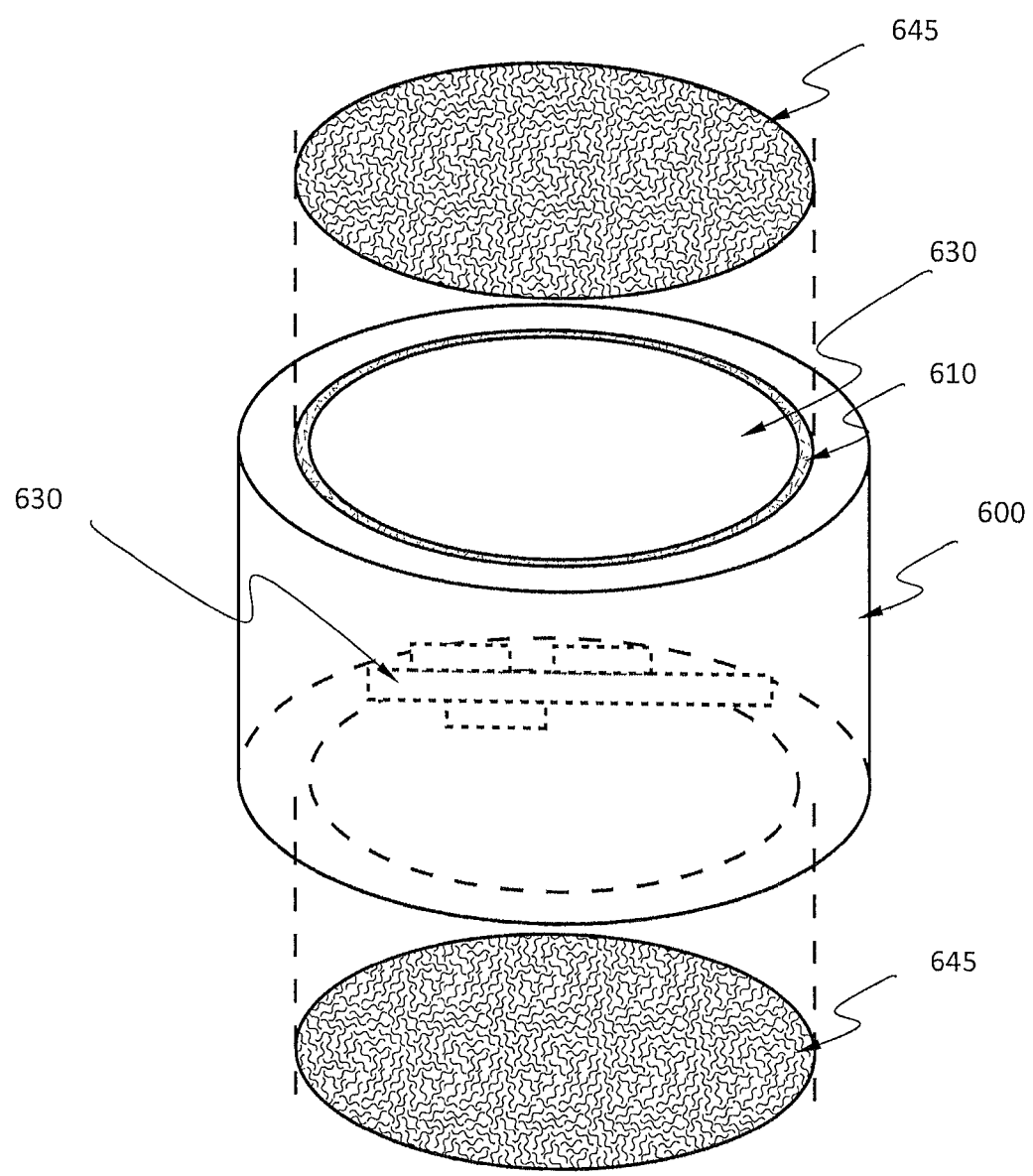
FIG. 6 depicts a schematic diagram of an implantable device, in accordance with various aspects and principles of the present disclosure.

FIG. 6 shows a frame 600 of an implantable device. The frame 600 may be a cylinder. Frame 600 may be formed of materials, and using any of the techniques, shown and described in reference to frame 100 of the embodiment of FIGS. 3A and 3B. Each of two end faces of the frame 600 may have an opening 640 and a ledge 610 that may be recessed from the end face. The ledge 610 may be configured to receive a film 645 such as the film 145 described herein. The film 645 and frame 600 may form a hermetical seal, thereby preventing direct contact of the internal components 630 mounted in frame 600 from water in the host.

Figure 7:
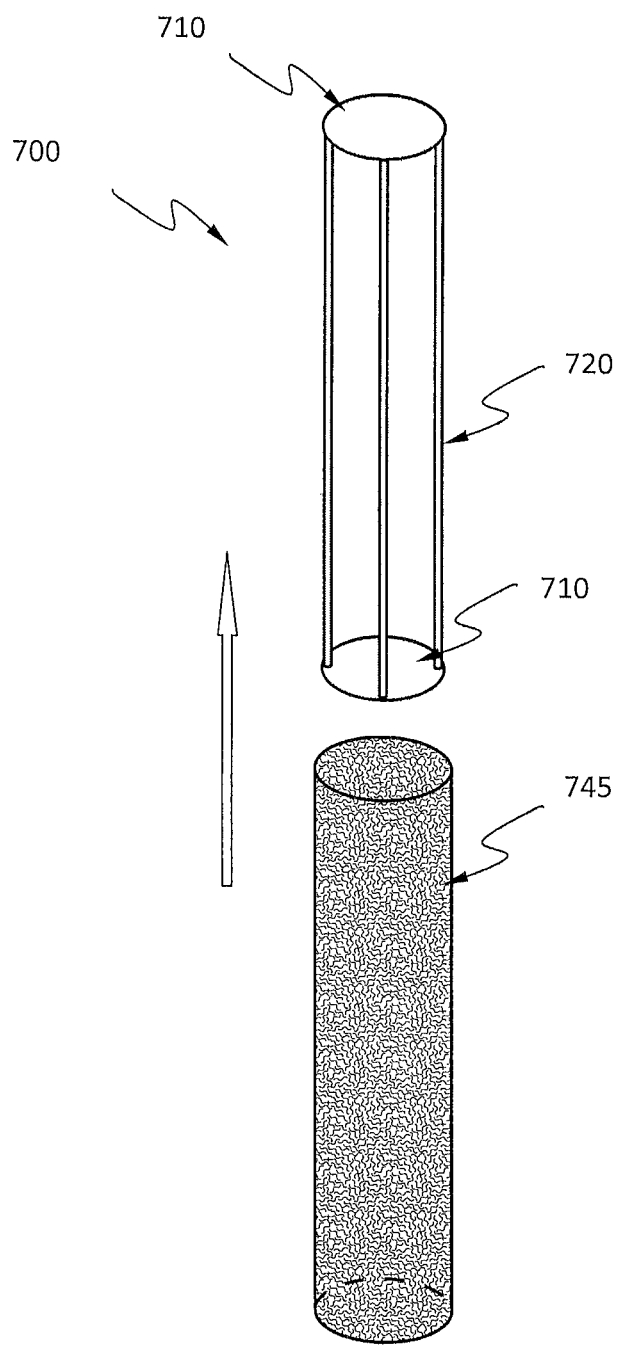
FIG. 7 depicts a schematic diagram of an implantable device, in accordance with various aspects and principles of the present disclosure.

FIG. 7 shows a frame 700 of an implantable device. The frame 700 may have two end pieces 710, optionally connected with each other by one or more connectors 720. These end pieces and/or connectors 720 may be formed of materials, and using any of the techniques, shown and described in reference to frame 100 of the embodiment of FIGS. 3A and 33. A film 745 such as the film 145 rolled into a cylinder may fit around the frame 700 and form a hermetical seal with the frame 700, thereby preventing direct contact of internal components mounted in frame 700 from water in the host. This film may be affixed to frame 700 using techniques described above. For instance, the film may be attached to frame 700 via an adhesive layer of the film (discussed above) that may be adhered to frame 700 via any combination of application of heating, application of pressure, and/or application of additional adhesive material. In some cases, film 745 need not be one piece, but may be separate pieces, each piece being provided to span between the two end pieces 710 and further span between adjacent connectors 720.

The implantable device disclosed herein may have small sizes. For example, the implantable device may have a surface with less than 2 cm$^2$ area. The implantable device may be injectable into the host through a syringe.

The descriptions above are intended to be illustrative, not limiting. For instance, examples described herein discuss implantable devices adapted to deliver electrical stimulation to a patient. However, the disclosure is not so limited. For instance, implantable devices adapted to deliver a therapeutic agent to a body instead of, or in addition to, electrical stimulation may usefully employ disclosed techniques. Such device may have a pump and a fluid reservoir instead of, or in addition to, stimulation generator 60. As another example, implantable devices adapted to deliver other types of stimulation instead of, or in addition to, electrical stimulation may employ disclosed techniques. Such devices may comprise those configured to deliver optical and/or magnetic stimulation. In yet other examples, devices need not deliver a therapy and may instead be provided solely to sense physiological signals. In yet other cases, the device may solely be provided to store data. For instance, small injectable devices may store a medical record that may be obtained transcutaneously via telemetry techniques, thereby making a patient's medical history transportable. Thus, many types of implantable device provided for many different purposes may employ techniques disclosed herein.

Moreover, although some techniques described herein focus on delivering therapy to a brain, medical devices that deliver therapy to any portion of an anatomy for any purpose, including to treat effects of a disease and/or trauma, may usefully employ techniques disclosed herein.

Thus, it will be apparent to one skilled in the art that modifications may be made to the embodiments as described without departing from the scope of the claims set out below.

What is claimed is:

1. A device, comprising:
   an electrically non-conductive frame;
   one or more electrical components disposed in the electrically non-conductive frame; and
   a self-supporting film;
   wherein the self-supporting film forms a hermetical seal with the electrically non-conductive frame,
   wherein the self-supporting film and the frame enclose the electrical components, and
   wherein the device is configured to be implanted into a live human or animal.

2. The device of claim 1, wherein the frame comprises one or more openings.

3. The device of claim 1, wherein the frame is ceramic, plastic or polymer composite.

4. The device of claim 1, wherein the frame comprises one or more feedthroughs, wherein the one or more feedthroughs are functional to accommodate signal pathways between the device and the live human or animal.

5. The device of claim 2, wherein the self-supporting film seals the one or more openings.

6. The device of claim 1, wherein the self-supporting film is water impermeable.

7. The device of claim 1, wherein exposed surfaces of the self-supporting film are bio-compatible.

8. The device of claim 1, wherein the self-supporting film is uniform in its composition or is a composite.

9. The device of claim 1, wherein the self-supporting film has a layered structure having two or more distinct layers.

10. The device of claim 1, wherein the self-supporting film comprises parylene C, silicone or a combination thereof.

11. The device of claim 1, wherein the self-supporting film comprises an adhesive layer.

12. The device of claim 1, wherein the self-supporting film is electrically non-conductive.

13. The device of claim 1, wherein the self-supporting film is flexible.

14. The device of claim 1, wherein the electrical components are configured to receive signals from a device outside the live human or animal, or transmit signals to a device outside the live human or animal, or both.

15. The device of claim 1, wherein the electrical components are embedded in a material.

16. The device of claim 15, wherein the material is thermally conductive.

17. The device of claim 4, wherein the device is entirely coated with a coating except the one or more feedthroughs.

18. The device of claim 17, wherein the coating is bio-compatible.

19. A method of making a device configured to be implanted into a live human or animal, comprising:
   providing an electrically non-conductive frame comprising one or more feedthroughs, one or more openings and a cavity;
   disposing one or more electrical components within the cavity;
   sealing the one or more openings by applying a self-supporting film to the one or more openings.

20. The method of claim 19, wherein self-supporting film is applied layer by layer.

21. The method of claim 19, further comprising coating the device except the one or more feedthroughs.

22. The method of claim 19, further comprising filling the cavity with a material to embed the electrical components in the material.

23. The device of claim 1, wherein the device comprises a surface with an area less than 2 cm².

24. The device of claim 1, wherein the device is injectable into the live human or animal through a syringe.

25. The device of claim 1, wherein the electrically non-conductive frame is free from an electrically conductive coating.

26. A device, comprising:
- a frame configured to provide mechanical support of the device;
- one or more electrical components configured to provide therapy to a live human or animal, to receive power from a device external to the live human or animal, to transmit data to a device external to the live human or animal, to receive data to a device external to the live human or animal, or any combination thereof; wherein the one or more electrical components are disposed in the frame; and
- a self-supporting film configured to protect the one or more electrical components from tissues of the live human or animal;
- wherein the device is configured to be implanted into the live human or animal.

27. The device of claim 26, wherein the self-supporting film and the frame enclose the one or more electrical components.

28. The device of claim 26, wherein the self-supporting film is water impermeable.

29. The device of claim 26, wherein exposed surfaces of the self-supporting film are bio-compatible.

30. The device of claim 26, wherein the self-supporting film is flexible.

* * * * *